United States Patent [19]

Aida et al.

[11] Patent Number: 4,620,546

[45] Date of Patent: Nov. 4, 1986

[54] ULTRASOUND HYPERTHERMIA APPARATUS

[75] Inventors: Satoshi Aida, Yokohama; Kenzo Matsumoto, Tokyo; Ayao Itoh, Yokohama; Yoshinori Suzuki, Yokohama; Kinya Takamizawa, Yokohama, all of Japan

[73] Assignee: Kabushiki Kaisha Toshiba, Kawasaki, Japan

[21] Appl. No.: 749,546

[22] Filed: Jun. 27, 1985

[30] Foreign Application Priority Data

Jun. 30, 1984 [JP] Japan ................... 59-135949
Jun. 30, 1984 [JP] Japan ................... 59-135973
Jun. 30, 1984 [JP] Japan ................... 59-135975

[51] Int. Cl.⁴ ........................................ A61B 10/00
[52] U.S. Cl. ................................. 128/660; 128/24 A
[58] Field of Search ........................... 128/660, 24 A

[56] References Cited

U.S. PATENT DOCUMENTS

| 3,771,355 | 11/1975 | Sachs ................... 128/663 X |
| 4,346,717 | 8/1982 | Hoerten ................. 128/660 |
| 4,368,410 | 1/1983 | Hance et al. ............ 128/24 A X |
| 4,385,634 | 5/1983 | Bowen .................. 128/660 X |
| 4,431,008 | 2/1984 | Wanner et al. .......... 128/660 |
| 4,501,277 | 2/1985 | Hongo .................. 128/663 X |

OTHER PUBLICATIONS

Ultrasound in Med. & Biol. vol. 9, No. 6, pp. 621-627 "Local Hyperthermia Induced by Focussed and Overlapping Ultrasonic Fields-An in vivo Demonstration" K. Hynynen et al. 1983.

IEEE Trans. BME vol. 31, No. 1, "Experience with a Multi-Transducer Ultrasound System for Localized Hyperthermia of Deep Tissues" P. Fessenden et al. 1984, pp. 126-135.

Primary Examiner—Kyle L. Howell
Assistant Examiner—Francis J. Jowarski
Attorney, Agent, or Firm—Oblon, Fisher, Spivak, McClelland & Maier

[57] ABSTRACT

An ultrasound hyperthermia apparatus has a tomographic ultrasound probe for obtaining a tomographic image and a heating applicator for heating a tumor portion. A position detector is provided to detect the positional relationship of the tomographic ultrasound probe and the heating applicator with respect to a living organism, and a hot spot detector detects the position of a focusing point, i.e., a hot spot of the ultrasound radiated from the heating applicator in accordance with position data from the position detector, thereby generating an image signal indicating the hot spot. The image signal indicating the hot spot is superimposed on a tomographic image signal, and the hot spot is displayed on a TV monitor together with the tomographic image.

13 Claims, 20 Drawing Figures

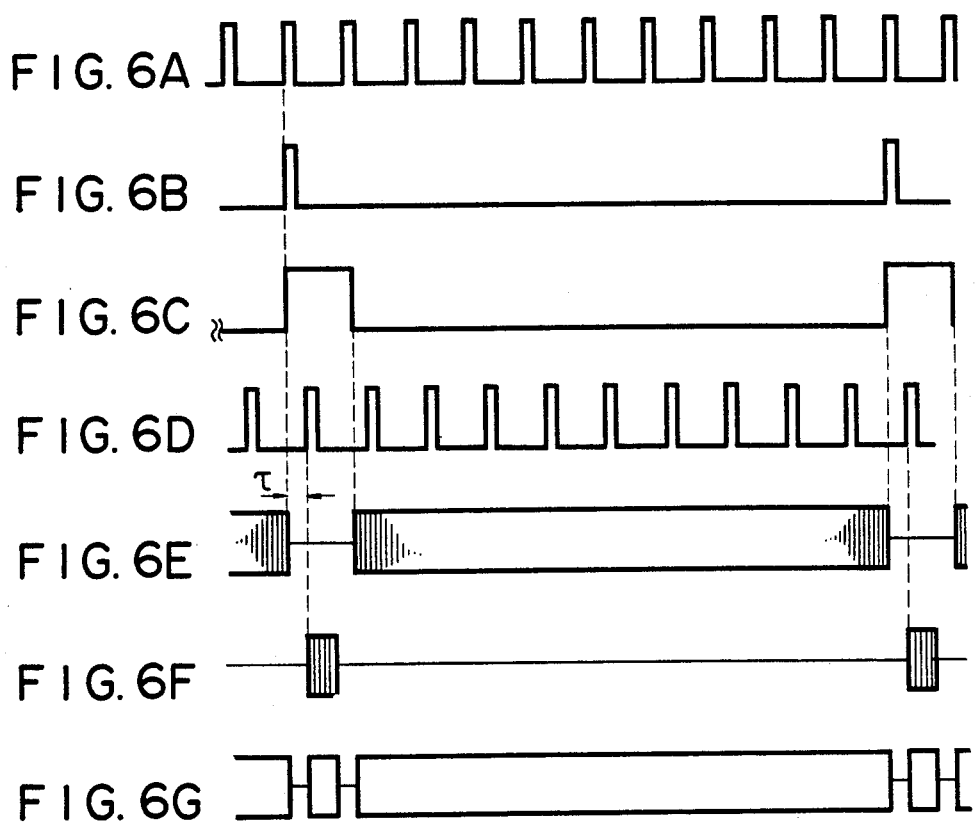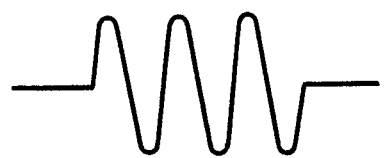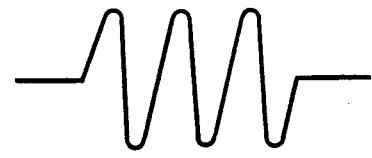

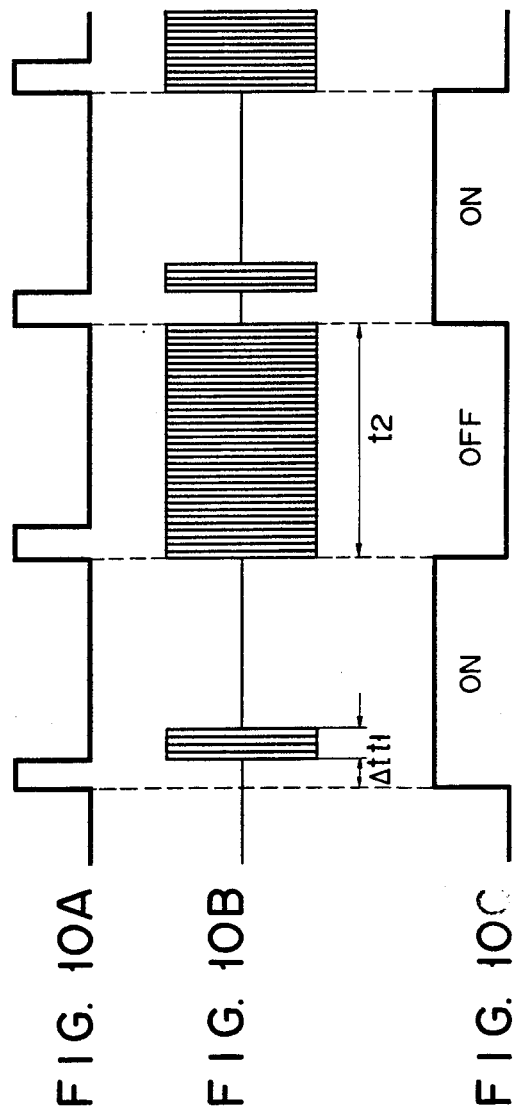

ULTRASOUND HYPERTHERMIA APPARATUS

BACKGROUND OF THE INVENTION

The present invention relates to an ultrasound hyperthermia apparatus which treats a tumor by a localized hyperthermia using ultrasound.

As therapies for a malignant tumor (i.e., a so-called cancer), surgical treatment, chemical treatment, radiotherapy and immunotherapy are employed. In addition to these therapies, a hyperthermia is currently receiving a lot of attention. The hyperthermia treats tumor cells by heating based upon the fact that the lethal temperature of tumor cells is lower than that of normal cells. It is considered that this therapy is effective for an unresectable tumor. Hyperthermia therapy is classified into whole body hyperthermia, regional hyperthermia and localized hyperthermia. Particularly, the localized hyperthermia in which a deep-lying tumor is selectively heated by focusing ultrasound thereon is receiving a lot of attention.

However, the conventional hyperthermia does not allow effective treatment since there is no way of knowing whether a tumor is in fact selectively heated.

SUMMARY OF THE INVENTION

It is an object of the present invention to provide an ultrasound hyperthermia apparatus which allows confirmation of a portion of a body heated by ultrasound.

It is another object of the present invention to provide an ultrasound hyperthermia apparatus which can selectively and effectively heat a desired area in a ultrasonic-tomogram of a living organism.

An ultrasonic hyperthermia apparatus according to the present invention comprises a tomographic ultrasonic probe for obtaining a tomogram of a living organism and a heating applicator for heating a desired portion in the living organism. Data indicating a focusing point of ultrasound or a hot spot heated by ultrasound from the heating applicator is obtained by position data of the heating applicator with respect to the tomographic probe or by detecting harmonic or large-amplitude components resulting from the heating ultrasound in an output signal of the tomographic ultrasonic probe. The focusing point of the heating ultrasound or heated portion is displayed on a display device together with a tomogram.

BRIEF DESCRIPTION OF THE DRAWINGS

FIGS. 6A to 6G are timing charts for explaining an operation of the apparatus of the embodiment shown in FIG. 3;

FIGS. 7A and 7B are waveform diagrams of an ultrasound for explaining a hot spot detecting operation;

FIGS. 10A to 10C are timing charts for explaining an operation of the apparatus shown in FIG. 9.

DETAILED DESCRIPTION OF THE PREFERRED EMBOIDMENTS

Figure 1:
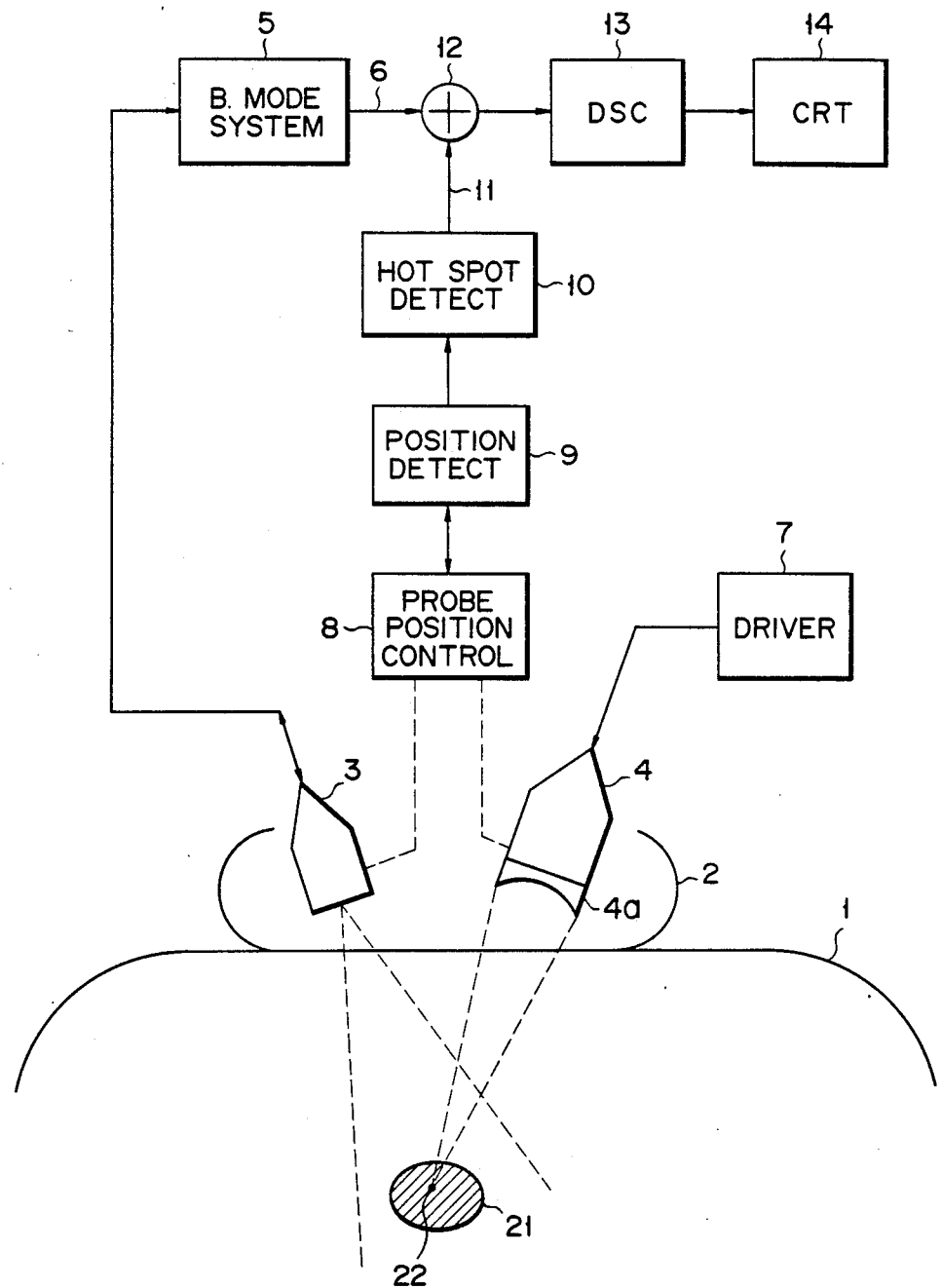
FIG. 1 shows an arrangement of an ultrasound hyperthermia apparatus according to an embodiment of the present invention.

An arrangement of an ultrasonic hyperthermia apparatus according to an embodiment of the present invention will be described with reference to FIG. 1. A water tank 2 is placed in contact with a surface of a living organism (patient) 1. A tomographic ultrasound probe 3 and a heating applicator 4 are arranged in the water tank 2. The water tank 2 is utilized to achieve acoustic impedance matching between the probe 3, the applicator 4 and the living organism 1 and to suppress an increase in the temperature of the surface of the living organism 1.

The probe 3 performs sector electronic scanning by means of a B mode system 5 so as to obtain tomographic image information of the living organism. The sector electronic scanning is well known in the field of ultrasonic diagnosis. When the probe 3 comprises array transducers, the B mode system 5 comprises a scanning circuit which performs focusing and deflection of a 3.5-MHz ultrasound beam by driving each transducer through a delay circuit, and a signal processing circuit which, after receiving a signal from each transducer through a delay circuit, obtains an image signal of a B mode image (tomographic image signal) through proper processing such as amplification, detection and the like.

The heating applicator 4 is driven by a driver 7 to continuously radiate a focused ultrasound beam having a relatively high energy and a frequency of, e.g., 500 kHz to 1 MHz, to a desired portion, i.e., a tumor portion of the living organism 1. In this embodiment, since the applicator 4 comprises an acoustic lens 4a at its end or is constituted by a concaved transducer, if the positional relationship of the applicator 4 with respect to the probe 3 is determined, the focusing position of the heating ultrasound in a B mode is uniquely, i.e., geometrically, determined. The probe 3 and the applicator 4 are supported by a probe position controller 8, and the position states thereof such as angles with respect to the surface of the living organism 1 are controlled. The controller 8 is connected to a position detector 9. The detector 9 comprises potentiometers interlocked with the probe 3 and the applicator 4, thereby detecting the positions of the probe 3 and the applicator 4, and the relative positions thereof.

Output information of the detector 9 is supplied to a hot spot detector 10. The detector 10 has a function for calculating the position of a hot spot, i.e., a focusing point (heated portion) of the heating ultrasound in the living organism 1. As described above, the hot spot of the ultrasound irradiated from the applicator 4 is geometrically determined by a positional state of the applicator 4. The detector 10 calculates the position of the hot spot in a scanning range (tomographic image) of the probe 3 in accordance with the relative position information of the probe 3 and the applicator 4 obtained by the position detector 9. The hot spot detector 10 generates a position information signal (a rectangular wave signal of a constant pulse width) 11 indicating the calculated hot-spot position at a time when the tomographic image signal corresponding to the heated portion is generated by the B mode system 5. The hot-spot detector 10 may comprise a read-only memory (ROM), from which is readout position information of the hot spot which is previously calculated in accordance with the positional relationship of the applicator 4 to the probe 3. When the positional relationship between the probe 4 and the probe 3 is changed by the controller 8, the focusing position of the ultrasound irradiated from the applicator 4 can be controlled.

The hot spot position information signal 11 is mixed with the tomographic image signal supplied from the B mode system 5 by an adder 12. Thus, in the tomographic image signal, a signal indicating the hot spot is superimposed on a tomographic signal component corresponding to the hot spot.

Figure 2A:
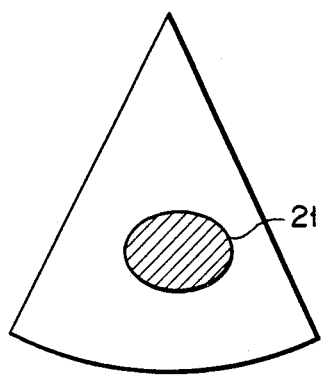
FIGS. 2A and 2B respectively show a normal tomogram and a tomogram on which a hot spot image is superimposed according to the present invention.
Figure 2B:
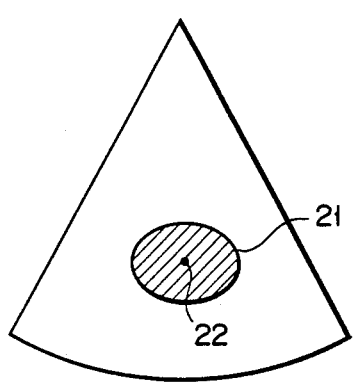

An output signal of the adder 12 is converted into a television video signal by a digital scan converter (DSC) 13, which is then applied to a television monitor (CRT) 14. FIG. 2A shows a tomographic image 21 obtained by the probe 3, and FIG. 2B shows a hot spot image 22 displayed on the screen of the TV monitor 14 together with the image 21 representing a tumor portion. In this case, it is preferred that the hot spot image be displayed by a luminescent spot brighter than normal images, or by a specific color, or by a specific symbol.

As described above, according to the present invention, information indicating the hot spot, i.e., the focusing position of the heating ultrasound is displayed on the tomographic image on the TV monitor. Therefore, the tumor portion can be selectively and effectively heated while observing the tomographic image on the TV monitor 14.

Even when a geometric focusing point of the heating ultrasound applicator is properly positioned at a tumor portion in the living organism before therapy, the relative position thereof may change due to a slight movement of the organism or refraction or reflection of the ultrasound. A second embodiment of the present invention which is arranged to precisely detect a hot spot without being influenced by body movement or refraction or reflection of the ultrasound will be described with reference to FIGS. 3 to 6. In this embodiment, a heating ultrasound generated by an ultrasound applicator and reflected in a living organism is received by a tomographic ultrasound probe, and a signal component having an amplitude higher than a predetermined amplitude or harmonic components of the heating ultrasound are detected from the received signal of the probe.

Figure 3:
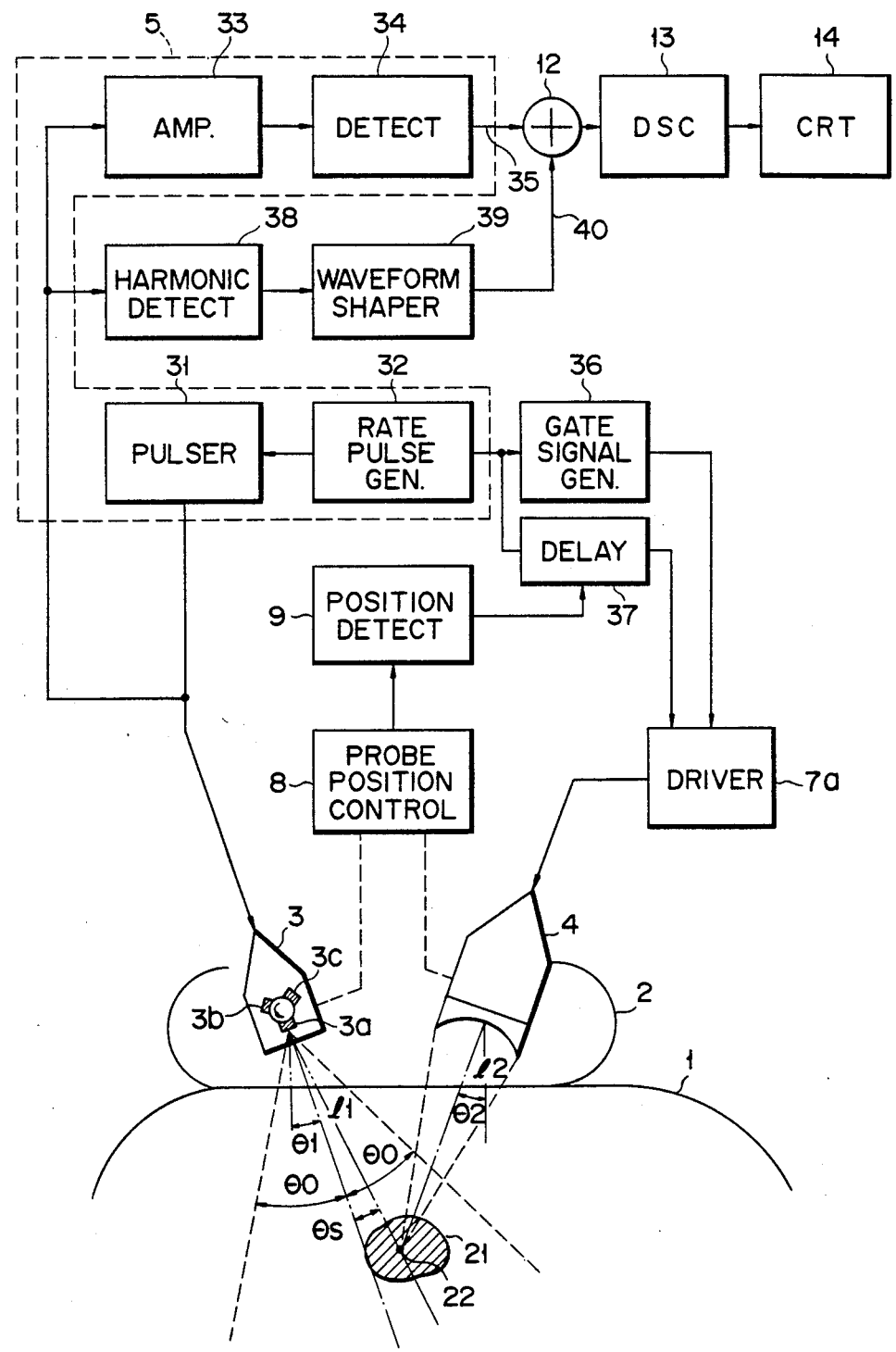
FIG. 3 shows an arrangement of an ultrasound hyperthermia apparatus according to another embodiment of the present invention.

FIG. 3 shows an arrangement of the ultrasound hyperthermia apparatus according to this embodiment. The same reference numerals as in FIG. 1 denote the same parts in FIG. 3. In this embodiment, a tomographic ultrasound probe 3 comprises three ultrasound transducers 3a, 3b and 3c fixed around a rotating member. Among these transducers, a transducer (3a in FIG. 3) facing a living organism 1 is driven by electric pulses supplied from a pulser 31 through a switching circuit (not shown) so as to emit pulsed ultrasound toward the living organism 1. The pulser 31 is intermittently driven at predetermined intervals by rate pulses from a rate pulse generator 32.

The ultrasound emitted by the ultrasound transducer 3a and reflected in the living organism 1 is received by the identical transducer 3a and is converted into an electric signal. The electric signal is derived as a tomographic image signal 35 through an amplifier 33 and a detector 34. Each of the transducers 3a, 3b and 3c performs transmission/reception of the ultrasound several hundreds of times while rotating within an angle range of $-\theta 0$ to $+\theta 0$, thereby obtaining the tomographic image signal 35 corresponding to a sector tomographic image. When the rotation angle of the transducer 3a exceeds $\theta 0$, the transducer 3b is driven by the pulser 31 through the switching circuit, and performs the same operation as in the transducer 3a. In this manner, the transducers 3a to 3c are sequentially driven, thereby continuously obtaining tomographic image signals 35.

The B mode system 5 in FIG. 1 comprises the pulser 31, the rate pulse generator 32, the amplifier 33 and the detector 34 in FIG. 3.

A heating applicator 4 has an acoustic lens or a concave transducer at its distal end in the same manner as in the previous embodiment. Thus, the focusing point of the ultrasound is uniquely determined in accordance with the position of the applicator 4. The applicator 4 is driven by a driver 7a. The driver 7a is provided mainly for supplying to the applicator 4 an electric signal having energy required for heating a tumor portion. However, in this embodiment, the driver 7a selectively supplies an electric signal of a continuous or burst wave.

Figure 4:
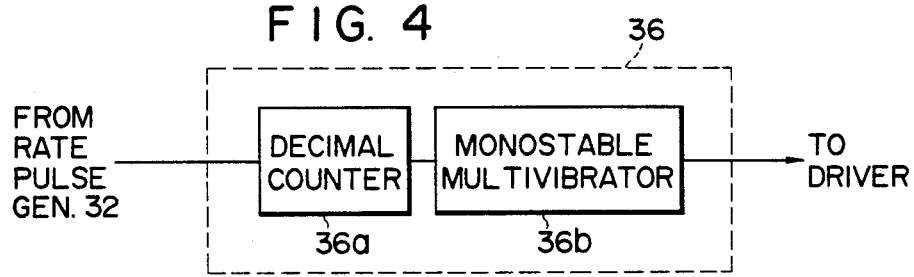
FIG. 4 shows an arrangement of a gate signal generator of FIG. 3.
Figure 5:
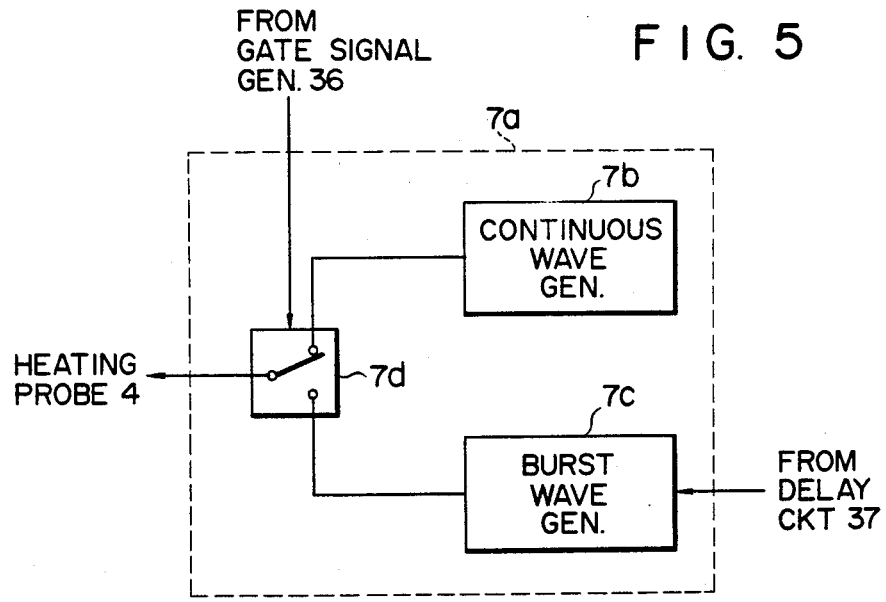
FIG. 5 shows an arrangement of a drive circuit of FIG. 3.

The driver 7a is responsive to a gate signal generator 36 and a delay circuit 37 which are connected to the generator 32 to selectively generate the burst or continuous wave signal. As shown in FIG. 4, the generator 36 comprises a decimal counter 36a for counting rate pulses (FIG. 6A) and a monostable multivibrator 36b for generating gate pulses (FIG. 6C) each having a duration substantially equal to one period of rate pulses when triggered by an output pulse (FIG. 6B) of the counter 36a. As shown in FIG. 5, the driver 7a comprises a continuous wave generator 7b, a burst wave generator 7c and a gate circuit 7d for connecting one of the generators 7b and 7c to the applicator 4.

The delay circuit 37 is responsive to the position detector 9 for delaying the rate pulses supplied to the driver 7a by a time of $\tau$, as shown in FIG. 6D. The delayed rate pulses trigger the generator 7c so as to generate the burst wave signal therefrom, as shown in FIG. 6F. In response to the gate signal, the gate circuit 7d selects the continuous or burst wave signal so as to drive the applicator 4. In an example of FIG. 6, when the gate signal is high, the gate circuit 7d selects the burst wave signal, otherwise, it selects the continuous wave signal.

The delay circuit 37 is provided so that the applicator 4 irradiates the burst ultrasound to the tumor at the same timing as the probe 3 does. The delay time $\tau$ provided by the delay cicuit 37 is set in accordance with the position information of the probe from the position detector 9 as follows:

$$\tau = (l1 - l2)/C$$

where l1 and l2 are distances between the probe 3 and the applicator 4 and the crossing point of central lines of the ultrasound beams generated therefrom, respectively, and C is the sound speed in the living organism. The distances l1 and l2 can be calculated from the central position (X1,Y1) of the probe 3 and an angle $\theta 1$ of the central line of the radiated ultrasound beam with respect to the living organism, the central position (X2,Y2) of the applicator 4 and an angle $\theta 2$ of the central line of the radiated ultrasound beam with respect to the living organism, and a deflection angle θs of the ultrasound beam by the probe 3.

The above description is applied when l1≧l2. When l1≦l2, the delay circuit 37 is connected between the generator 32 and the pulser 31.

In order to detect the focusing point of the ultrasound from the applicator 4, a reception signal received by the probe 3 is supplied to a harmonic wave detector 38. The harmonic wave detector may be comprised of a band-pass filter, which extracts from the output signal of the probe 3 harmonic components of ultrasound radiated by the applicator 4, thus detecting the hot spot. For example, the frequency of the ultrasound radiated by the applicator 4 is 500 kHz, and the frequency of the ultrasound radiated by the probe 3 is 3 MHz. Thus, it will be understood that a reception frequency band of the probe 3 can cover the harmonics of the heating ultrasound frequency.

Generally, when ultrasound propagates in a medium (e.g., tissue), the waveform of the ultrasound is distorted as the sound pressure thereof increases. A sonic speed in the medium depends upon the sound pressure. Assuming that a sonic speed of sound wave having a small sound pressure is represented by C0 and a particle velocity is represented by v, the sonic speed C of the sound wave having a finite sound pressure amplitude is given by $$C = C0 + \beta v$$

where $\beta$ is a constant.

That is, when v>0, C>C0, and when v<C0, C<C0. Therefore, when the ultrasound having a waveform shown in FIG. 7A propagates in the medium, waveform distortion as shown in FIG. 7B occurs. In other words, harmonic components are formed by waveform distortion. In the ultrasonic hyperthermia, since the ultrasound is focused on the heated portion, such non-linear distortion of the ultrasound easily occurs. In this embodiment, the hot spot is detected by utilizing such a characteristic of the ultrasound.

More specifically, the maximum amplitude of the harmonic components corresponds to the hot spot. Therefore, an output signal of the detector 38 is converted into a rectangular wave by a waveform shaper 39. The rectangular waveform signal 40, as a hot spot display signal, is synthesized with the tomographic image signal 35 by the adder 12. The hot spot is displayed on the TV monitor 14 together with the tomographic image in the same manner as in the above embodiment.

In this embodiment, although the harmonic detector 38 is provided, it can be omitted for the following reason. Generally, a resonant frequency of a transducer of a tomographic ultrasonic probe is set to 3 MHz or higher in order to obtain a good tomographic image. Meanwhile, in order to achieve effective heating, the heating application 4 is desired to produce ultrasound of 1 MHz or lower. Therefore, in this case, even if the heating ultrasound reaches the probe 3, the fundamental wave or lower harmonics cannot substantially be detected, and harmonic components from the heated portion only are detected. In this manner, harmonic components can be detected utilizing the filter function of the probe 3 without providing a harmonic detector.

Figure 8:
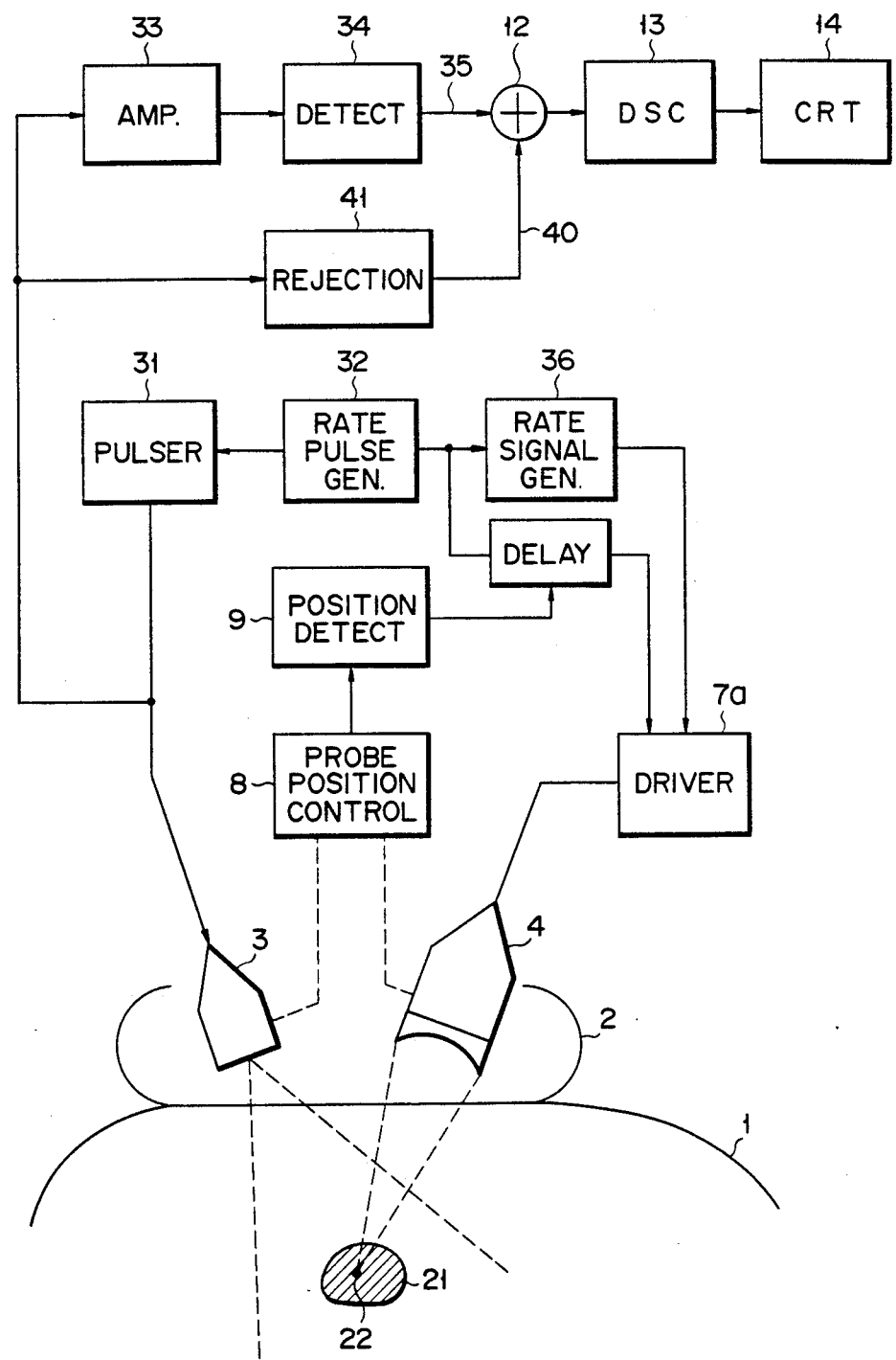
FIG. 8 shows an arrangement of an ultrasound hyperthermia apparatus according to still another embodiment of the present invention.

Still another embodiment of the present invention will be described with reference to FIG. 8. In this embodiment, a rejection circuit 41 is provided in place of the harmonic detector 38 and the waveform shaper 39 in the embodiment shown in FIG. 3. The heating ultrasound has a high energy level, as is the amplitude of its reflection wave. For this reason, the rejection circuit 41 which detects components having an amplitude larger than a predetermined amplitude from an output signal of tomographic ultrasonic probe 3 can detect a hot spot.

Figure 9:
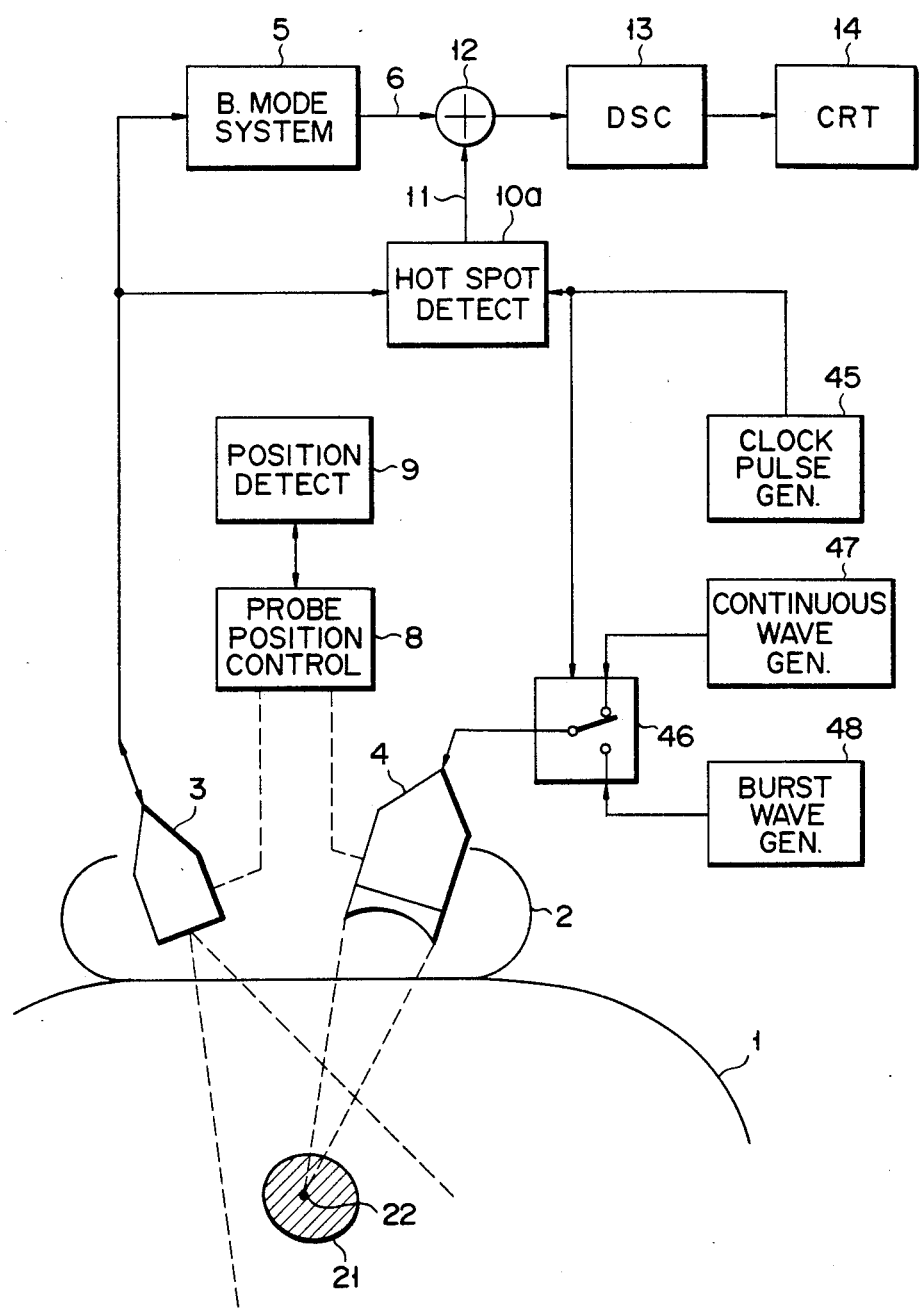
FIG. 9 shows an arrangement of an ultrasound hyperthermia apparatus according to still another embodiment of the present invention.

Still another embodiment of the present invention will be described with reference to FIG. 9. In FIG. 9, the same reference numerals as in the above embodiment denote the same parts in this embodiment. A continuous wave generator 47 and a burst wave generator 48 are provided. A switch 46 is provided which is responsive to a clock pulse generator 45 for selectively connecting one of generators 47 and 48 to heating applicator 4. As a result, the applicator 4 radiates a continuous (or burst) ultrasound beam, having a relatively large energy level, onto tumor portion 21 in living organism 1.

The clock pulse generator 45 controls a hot spot detector 10a. The detector 10a detects the hot spot 22 in the living organism 1 in response to an output signal of the probe 3. The hot spot is detected based upon harmonic components or maximum amplitude components of the ultrasound from the applicator 4 in the same manner as in the above embodiments. The detector 10a is controlled by clock pulses from the generator 45.

FIGS. 10A to 10C are timing charts of the clock pulses from the generator 45, a drive signal supplied to the applicator 4, and an operating state of the detector 10a, respectively. FIG. 10A shows a waveform of the clock pulses. FIG. 10B shows the drive signal of the applicator 4. The applicator 4 is driven by the burst wave during a time period of t1 and by the continuous wave during a time period of t2. FIG. 10C shows the operating state of the hot spot detector 10a. As shown, the detector 10a is turned on or off in synchronism with the rising or falling edge of the clock pulses at an interval of one period thereof.

As shown in FIGS. 10A to 10C, the detector 10a is turned on in response to the rising edge of the first clock pulse. After the lapse of a time Δt, the burst wave drive signal is supplied to the applicator 4 through switching circuit 46, thus causing radiation of the burst ultrasound therefrom. The burst ultrasound is radiated to the tumor of the living organism, and the harmonic components are formed as described above. The harmonic components are detected by the detector 10a which is in the ON state.

The detector 10a is turned off in synchronism with the rising edge of the next clock pulse, and the continuous wave drive signal is supplied to the applicator 4 through the switching circuit 46. Thus, the continuous ultrasound is radiated which contributes to the heating of the tumor. In this manner, the detecting operation and the heating operation are repeated at an interval of the period of the clock pulses.

The hot spot detector 10a provides a hot spot display signal 11 when the harmonic components of the output signal of the probe 3 reach the maximum amplitude. The hot spot display signal 11 is synthesized with a tomographic image signal 6 from B mode system 5 by an adder 12. The synthesized signal is converted into a TV signal by a digital scan converter 13 and then visually displayed on a TV monitor 14.

In order to obtain a tomographic image, a linear electronic scanning method can be utilized in addition to a sector electronic scanning method and a mechanical scanning method. In order to focus the ultrasound, means other than an acoustic lens can be utilized.

What is claimed is:

1. An ultrasound hyperthermia apparatus comprising:
   a tomographic ultrasound probe for irradiating a living organism with ultrasound and for receiving reflected ultrasound therefrom in order to obtain a tomographic image of the living organism;
   a heating applicator for irradiating a desired portion in the living organism with focused ultrasound so as to heat the desired portion;
   tomographic image signal generating means, coupled to said tomographic ultrasound probe, for generating a tomographic image signal representative of reflected signal intensity of said reflected ultrasound;
   focusing point detecting means, coupled to said heating applicator, for detecting the position of a focusing point of the heating ultrasound to generate a focusing point position information signal indicating the position of the focusing point of the ultrasound; and
   tomographic image display means, coupled to said focusing point detecting means and said tomographic image signal generating means, for displaying the tomographic image and the focusing point of the ultrasound in the tomographic image.

2. An apparatus according according to claim 1, wherein said heating applicator comprises means for focusing the radiated ultrasound at an end thereof.

3. An apparatus according to claim 1, wherein said tomographic image signal generating means comprises a B mode system.

4. An apparatus according to claim 1, wherein said tomographic image display means comprises a digital scan converter and a CRT display.

5. An ultrasound hyperthermia apparatus comprising:
   a tomographic ultrasound probe for irradiating a living organism with ultrasound and for receiving reflected ultrasound therefrom in order to obtain a tomographic image of the living organism;
   a heating applicator for irradiating a desired portion in the living organism with focused ultrasound so as to heat the desired portion;
   tomographic image signal generating means, coupled to said tomographic ultrasound probe, for generating a tomographic image signal representative of reflected signal intensity of said reflected ultrasound;
   heat portion detecting means, coupled to said tomographic ultrasound probe, for detecting a heated portion in the living organism based upon the ultrasound radiated from said heating applicator so as to generate a heated portion position information signal indicating the position of the heated portion; and
   tomographic image display means, coupled to said heated portion detecting means and said tomographic image signal generating means, for displaying the tomographic image and the heated portion in the tomographic image.

6. An apparatus according to claim 5, wherein said heated portion detecting means is arranged to detect, from an output signal of said tomographic ultrasound probe, harmonic components of the ultrasound from said heating applicator in order to detect the heated portion.

7. An apparatus according to claim 5, wherein said heated portion detecting means is arranged to detect, from an output signal of said tomographic ultrasound probe, an amplitude component of the ultrasound from said heating applicator larger than an amplitude component of the ultrasound from said tomographic ultrasound probe in order to detect the heated portion.

8. An apparatus according to claim 5, wherein said heating applicator is arranged to be driven by a continuous wave drive signal in order to heat an internal area of the living organism and to be driven by a burst wave drive signal in order to detect the heated portion.

9. An apparatus according to claim 8, wherein said heating applicator is alternately driven by the continuous wave drive signal and the burst wave drive signal.

10. An apparatus according to claim 5, further comprising timing means for causing said heating applicator and said tomographic ultrasonic probe to radiate the ultrasound at substantially the same timing, to a portion to be heated.

11. An ultrasound hyperthermia apparatus comprising:
    a tomographic ultrasound probe for irradiating a living organism with ultrasound and for receiving reflected ultrasound therefrom in order to obtain a tomographic image of the living organism;
    a heating applicator for irradiating a desired portion in the living organism with focused ultrasound so as to heat the desired portion;
    tomographic image signal generating means, coupled to said tomographic ultrasound probe, for generating a tomographic image signal representative of reflected signal intenisity of said reflected ultrasound;
    heat portion detecting means, coupled to said tomographic ultrasound probe, for detecting a heated portion in the living organism based upon burst wave ultrasound radiated from said heating applicator so as to generate a heated portion position information signal indicating the position of the heated portion; and
    tomographic image display means, coupled to said heated portion detecting means and said tomographic image signal generating means, for displaying the tomographic image and the heated portion in the tomographic image.

12. An apparatus according to claim to claim 11, wherein said heated portion detecting means is arranged to detect, from an output signal of said tomographic ultrasound probe, harmonic components of the ultrasound radiated from said heating applicator in synchronism with radiation of burst wave ultrasound from said heating applicator.

13. An apparatus according to claim 11, wherein said heated portion detecting means is arranged to detect, from an output signal of said tomographic ultrasonic probe, signal components having an amplitude larger than a predetermined amplitude based upon the ultrasound radiated from said heating applicator in synchronism with radiation of burst wave ultrasound from said heating applicator.

* * * * *